United States Patent [19]
Kohler et al.

[11] Patent Number: 5,711,959
[45] Date of Patent: Jan. 27, 1998

[54] BIOCOMPATIBLE MATERIALS

[75] Inventors: Anja S. Kohler, Stillwater; Daniel L. Mooradian, Eagan; Leo T. Furcht, Minneapolis, all of Minn.

[73] Assignee: Regents of the University of Minnesota, Minneapolis, Minn.

[21] Appl. No.: 707,954

[22] Filed: Sep. 10, 1996

Related U.S. Application Data

[63] Continuation of Ser. No. 406,124, Mar. 17, 1995, abandoned.

[51] Int. Cl.$^6$ ............................................. A61F 2/02
[52] U.S. Cl. ........................ 424/423; 514/822; 523/112; 523/113
[58] Field of Search .................... 424/423; 514/822; 523/112, 113

[56] References Cited

U.S. PATENT DOCUMENTS

| | | | |
|---|---|---|---|
| 4,480,041 | 10/1984 | Myles et al. | 436/508 |
| 4,927,879 | 5/1990 | Pidgeon | 525/54 |
| 4,931,498 | 6/1990 | Pidgeon | 525/54 |
| 4,973,493 | 11/1990 | Guire | 427/2 |
| 4,979,959 | 12/1990 | Guire | 623/66 |
| 5,217,743 | 6/1993 | Farah | 427/2 |
| 5,256,641 | 10/1993 | Yatvin et al. | 514/2 |

FOREIGN PATENT DOCUMENTS

| | | |
|---|---|---|
| 92/06719 | 4/1992 | United Kingdom. |
| WO85/03295 | 8/1985 | WIPO. |
| WO90/09384 | 8/1990 | WIPO. |
| WO91/13639 | 9/1991 | WIPO. |
| WO92/07858 | 5/1992 | WIPO. |

OTHER PUBLICATIONS

J.D. Andrade, et al., "Surfaces and Blood Compatability, Current Hypotheses" *Trans. Am. Soc. Artif. Intern. Organs*, 75–84 (1987).

L.I. Barsukov, et al., "Affinity Chromatography of the Phosphatidylcholine Exchange Protein from Bovine Liver," *Biochimica et Biophysica Acta*, 513, 198–204 (1978).

L.D. Bergelson (ed.), *Lipid Biochemical Preparations*, 267–269 (1980).

Ewan J. Campbell, et al., "Biocompatible Surfaces Using Methacryloylphosphorylcholine Laurylmethacrylate Copolymer," *ASAIO Journal*, M853–M857 (1994).

James A. Hayward, et al., "Biomembrane surfaces as models for polymer design: the potential for haemocompatibility," *Biomaterials*, 5, 135–141 (May 1984).

(List continued on next page.)

*Primary Examiner*—Carlos Azpuru
*Attorney, Agent, or Firm*—Mueting, Raasch, Gebhardt & Schwappach, P.A.

[57] ABSTRACT

A biocompatible material comprising a substrate and a phospholipid moiety covalently attached thereto in an amount and orientation effective to provide an improved nonthrombogenic surface relative to the substrate without the phospholipid moiety covalently attached thereto is provided. In particularly preferred embodiments, the biocompatible material has the following structure:

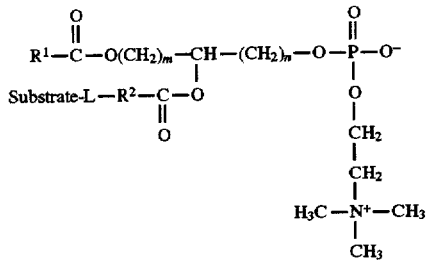

wherein: $R^1$ is a $(C_1-C_{30})$alkyl group; $R^2$ is a $(C_1-C_{30})$ alkylene group; m is 1–4; n is 1–4; and L is a divalent linking group covalently bonded to the substrate and to the phospholipid moiety.

13 Claims, 8 Drawing Sheets

OTHER PUBLICATIONS

Kazuhiko Ishihara, et al., "Reduced thrombogenicity of polymers having phospholipid polar groups," *Journal of Biomedical Materials Research*, 24, 1069–1077 (1990).

Kazuhiko Ishihara, et al., "Hemocompatibility of human whole blood on polymers with a phospholipid polar group and its mechanism," *Journal of Biomedical Materials Research*, 26, 1543–1552 (1992).

Robert J. Markovich, et al., "Silica Subsurface Amine Effect on the Chemical Stability and Chromatographic Properties of End–Capped Immobilized Artificial Membrane Surfaces," *Anal. Chem.*, 63, 1851–1860 (1991).

Charles Pidgeon et al., "Immobilized Artificial Membrane Chromatography: Rapid Purification of Functional Membrane Proteins," *Analytical Biochemistry*, 194. 163–173 (1991).

Tomoko Ueda, et al., "Protein adsorption on biomedical polymers with a phosphorylcholine moiety adsorbed with phospholipid," *J. Biomater, Sci. Polymer Edn.*, 3, 185–194 (1991).

J. Yu, et al., "Polymeric biomaterials: influence of phosphorylcholine polar groups on protein adsorption and complement activation," *The International Journal of Artificial Organs*, 17, 499–504 (1994).

BIOCOMPATIBLE MATERIALS

This is continuation of application Ser. No. 08/406,124, filed Mar. 17, 1995, now abandoned.

STATEMENT OF GOVERNMENT RIGHTS

The present invention was made with the support of the United States Government via grants from the National Institute of Health (Grant Nos. R37-CA2463 and R01-EY09065. The government has certain rights in the invention.

FIELD OF THE INVENTION

The present invention relates generally to biocompatible materials. More specifically, the present invention relates to biocompatible materials having a covalently bound phospholipid moiety. The materials produced in accordance with the invention have various medical applications, such as in medical devices, surgical equipment, vascular grafts, etc.

BACKGROUND OF THE INVENTION

The implantation of vascular grafts and medical devices such as artificial organs, artificial heart valves, artificial joints, synthetic and intraocular lenses, electrodes, catheters, and various other prosthetic devices into or on the body is a rapidly developing area of medicine. However, this has been hampered by the lack of suitable synthetic materials that are stable when contacted with physiological fluids, particularly blood.

Adverse reactions between materials and blood components are predominant factors limiting the use of synthetic materials that come into contact with physiological fluids. For example, catheters, vascular grafts, and the like, tend to serve as a nidus, or focus, for the formation of thrombi (blood clots). Initial contact of such materials with blood results in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion. As a result, the continual use of anticoagulants in conjunction with the introduction of such materials to the body is often necessary.

Furthermore, complement activation occurs when materials are introduced into blood. Adsorption of large amounts of IgG, IgM, and C3b onto surfaces causes activation. Subsequently, complexes may be formed which contribute to undesirable immune responses, such as proteolysis, cell lysis, opsonization, anaphylaxis, and chemotaxis. As a result, these responses render such materials incompatible with the living body.

A number of approaches have been suggested to improve the biocompatibility of medical devices. One approach has been to modify the surface of the material to prevent undesirable protein adhesion by providing the material with a low polarity surface, a negatively charged surface, or a surface coated with biological materials, such as enzymes, endothelial cells, and proteins. Another approach has been to bind anticoagulants to the surface of biologically inert materials to impart antithrombogenic characteristics to the materials. Still another approach used in the art has been the copolymerization of various phospholipids which are used as coating materials for various substrates. Partial polymeric backbone coatings have also been used in a similar fashion. However, many of these methods can result in a leaching or "stripping off" of the coating.

Additionally, quaternary amines have been bound to polymer surfaces, followed by the binding of heparin thereto. Conversely, heparin has been complexed with a quaternary amine prior to coating the complex onto a polymeric surface. Both of these methods have the disadvantage of being nonpermanent or leachable systems, i.e., the heparin would gradually be lost from the polymer material into the surrounding medium. Furthermore, coated systems generally have limited viability due to the instability of the anticoagulant.

Thus, a need exists for a biocompatible material for use in medical devices that retains antithrombogenic properties, i.e., reduced platelet adhesion and activation, for an extended period of time.

SUMMARY OF THE INVENTION

The invention provides a biocompatible material comprising a substrate and a phospholipid moiety covalently attached thereto in an amount and orientation effective to provide an improved nonthrombogenic surface relative to the substrate without the phospholipid moiety covalently attached thereto. Preferably, the phospholipid moiety contains a choline moiety and a phosphate polar group. More preferably, the phospholipid moiety has the following structure:

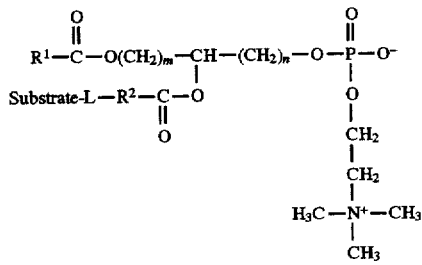

wherein: $R^1$ is a $(C_1-C_{30})$alkyl group; $R^2$ is a $(C_1-C_{30})$ alkylene group; m is 1–4; n is 1–4; and L is a divalent linking group, preferably containing an amide functionality, covalently bonded to the substrate and to the phospholipid moiety.

The present invention is also directed to biocompatible medical devices comprising substrates which have been modified with a covalently bound phospholipid moiety, such as a phosphatidylcholine moiety.

The materials modified in accordance with the present invention are prepared by covalently attaching a phospholipid moiety to the substrate material by initially derivatizing at least one fatty acid chain of a phospholipid of the following formula:

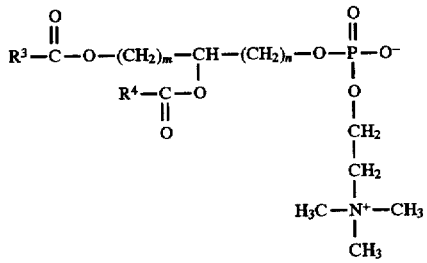

wherein: $R^3$ is a $(C_1-C_{30})$alkyl group having 0–4 double bonds; $R^4$ is a $(C_1-C_{30})$alkyl group having 0–4 double bonds; m is 1–4; n is 1–4; and either $R^3$ or $R^4$ has at least one double bond. The derivatized phospholipid, preferably a carboxylated phospholipid, is then reacted with a modified substrate, preferably an aminated substrate, to form a covalent linkage. Once modified, the resulting product exhibits improved biocompatibility.

DETAILED DESCRIPTION OF THE INVENTION

Figure 1:
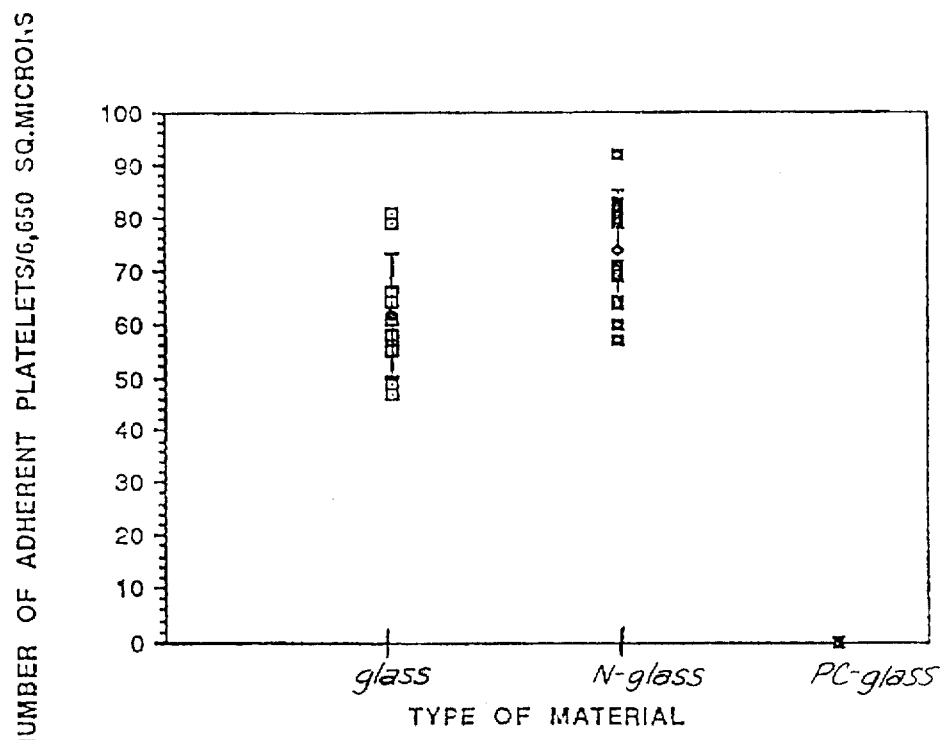
FIG. 1 is a graph illustrating the number of adherent platelets to various material substrates, the materials shown being unmodified surface materials as compared to those modified in accordance with the invention. The substrates are glass, aminated glass (N-glass), and phosphatidylcholine-grafted glass (PC-glass).

The biocompatibility of materials used in medical devices or other implantable materials or materials that are not necessarily implanted but that come into contact with blood is improved by covalently attaching a phospholipid moiety, e.g., a phosphatidylcholine moiety. By covalently attaching a phospholipid moiety to a substrate, the extent and severity of adverse reactions between the substrate and blood is reduced. The term "biocompatible" as used herein means that the material shows reduced platelet adhesion or spreading upon interaction with blood when compared to the material without the phospholipid.

Blood compatibility is much more complex than the compatibility of a material with other bodily fluids or tissues. This is because of the complex mixture of red cells, white cells, platelets, inorganic ions, and plasma proteins such as albumins, fibrinogens, and globulins in blood. Blood forms a clot or thrombus when injury occurs or when it is contacted by a foreign substance. Almost all materials set off this clot-forming process, and generally soon thereafter become coated with an irreversible clot of varying size. Such clots could have an adverse effect on the utility of such materials. Thus, particularly preferred biocompatible materials of the present invention are particularly advantageous because they do not cause any significant coagulation or reaction of natural blood components as would occur in vivo, such as blood platelet adhesion and activation.

The biocompatible materials of the present invention include a substrate and a phospholipid moiety covalently attached thereto in an amount and orientation effective to provide an improved nonthrombogenic surface relative to the substrate without the phospholipid moiety covalently attached thereto. By this it is meant that for a substrate to which there is a phospholipid moiety covalently attached, there is a reduction in the number of platelets attached to the substrate surface per unit area relative to the same substrate without the phospholipid moiety covalently attached thereto. Preferably, there is at least a 50% reduction in the number of adherent platelets per unit area of the substrate surface upon covalently attaching the phospholipid moiety. More preferably, there is at least an 80% reduction in the number of adherent platelets per unit area of substrate surface when a phospholipid is covalently attached to the substrate. Even more preferable is a 90% reduction in the number of adherent platelets per unit area of substrate surface when a phospholipid is covalently attached to the substrate. Most preferably, the substrate surface is substantially nonthrombogenic, i.e., it causes little or no platelet adhesion to occur.

In particularly preferred embodiments, the biocompatible materials of the present invention cause little or no platelet activation, in addition to low platelet adhesion, as determined by platelet spread. That is, for substrates to which platelets do adhere, the platelets generally remain rounded and exhibit little or no spreading. Thus, there is little thrombosis that can occur. The biocompatible materials of the present invention are particularly advantageous because they do not cause significant thrombosis, even though protein deposition occurs. That is, although fibrinogen adsorbs to the surface of the substrates to which a phospholipid is covalently attached, the fibrinogen is not present in an orientation that causes adverse platelet adhesion and activation.

Substrates to which the phospholipid can be attached in accordance with the invention include any synthetic or natural material that is insoluble in physiological fluids. It can be a metal such as titanium or stainless steel, glasses such as soda glass and silica glass, inorganic materials, and organic polymers. Preferably, it is an organic polymer that has demonstrated its relative biocompatibility for use in various medical devices. Examples of polymeric substrates useful for the invention are synthetic polymers such as polyurethanes, polycarbonates, silicone elastomers, polypropylene, polyethylene, polyvinyl chlorides, polyesters, nylons, polyvinyl pyrrolidones, polymethacrylates such as polymethylmethacrylate (PMMA), n-Butyl cyanoacrylate, polyvinyl alcohols, cellulosics, polyvinylidene fluoride (PVDF), polytetrafluoroethylene, polytetrafluoroethylene(polyester), ethylene tetrafluoroethylene copolymer (ETFE), acrylonitrile butadiene ethylene, polyamide, polyimide, styrene acrylonitrile, and the like. As long as the substrate can be modified, as by amination for example, for covalent attachment of the phospholipid, it can be used as a substrate.

Among the polyurethanes suitable for use in the present invention are the elastomeric, segmented polyether polyurethanes derived from repeating units of polytetramethylene ether glycol and a mixture of methylene diisocyanate and a diol (or diamine) coupler. Examples of commercially available polyurethanes include, for example, those with the designation TYGOTHANE from Norton Chemical Co., Akron, Ohio, RENATHANE from Renal Systems, Inc., Minneapolis, Minn., and TECOFLEX from Thermedic, Inc., Woburn, Mass. Among the silicone elastomers suitable for use in the present invention are the medical grade elastomers such as the silicone elastomer commercially available under the designation SILASTIC from Dow Corning Corp., Midland, Mich. Among the polycarbonates suitable for use in the present invention are the bisphenol A polycarbonates such as the one commercially available under the designation LEXAN from General Electric, Pittsfield, Mass.

Preferably, the phospholipid moiety attached to the biocompatible materials of the present invention contains a choline moiety and phosphate polar group and variable lengths of fatty acid chains. That is, the phospholipids are derivatives of phosphatidylcholine. Particularly preferred such biocompatible materials are represented by the following structure:

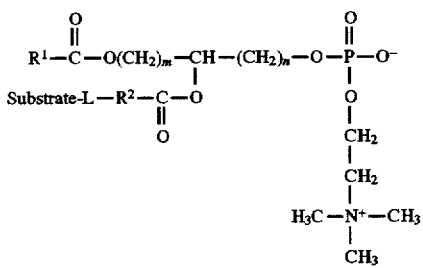

wherein: $R^1$ is a $(C_1-C_{30})$alkyl group; $R^2$ is a $(C_1-C_{30})$ alkylene group; m is 1–4; n is 1–4; and L is a divalent linking group covalently bonded to the substrate and to the phospholipid moiety. Most preferably, $R^1$ is a $(C_{12}-C_{20})$alkyl group; $R^2$ is a $(C_4-C_{10})$alkylene group; m is 1; and n is 1.

It should be understood that this representation does not mean that there is only one phospholipid moiety attached to the substrate. Rather, the phospholipid moiety attached to the substrate through the linking group L is present on the substrate in an amount effective to improve the nonthrombogenic characteristics of the substrate surface. Furthermore, it should be understood that the biocompatible materials of the present invention can include one or more types of phospholipid moieties covalently attached to the same substrate. That is, more than one type of phospholipid moiety can be covalently attached to any one substrate surface.

The phospholipid moieties are attached to the substrates in a manner such that the polar head groups, i.e., the phosphate end of the molecules, are exposed at the substrate surface. This is accomplished by covalently attaching at least one of the fatty acid chains of the phospholipid molecules to the substrate. Preferably, only one of the fatty acid chains of each phospholipid molecule is covalently attached to the substrate. In this way, there is one fatty acid chain free per phospholipid moiety to provide advantageous surface properties. This can be accomplished by any number of conventional methods known in the art using suitable crosslinking agents.

The covalent linkage occurs through a divalent linking group that is covalently bonded to the substrate and covalently bonded to the phospholipid moiety. This can be accomplished through a variety of functionalities depending on the functionality of the phospholipid and the substrate at the attachment sites of each. As long as a covalent linkage is accomplished, there is no criticality to the type of divalent linking group used. Typically, divalent linking groups include amide functionalities. Other linking groups may also be used, such as esters, acyl halides, alkyl halides, sulfones, sulfoxides, sulfide linkages and the like. A preferred amide-containing linking group is —C(O)—NH—(CH$_2$)$_p$— wherein p is 0–20, preferably p is 1–6. This linkage can occur by incorporating a crosslinking agent into the linking group between the substrate and the phospholipid, or the crosslinking agent can be used as a template to activate the substrate and phospholipid functionalities to interact.

For example, phosphatidylcholine can be attached to a silica substrate through an amide linkage as shown in the following structure:

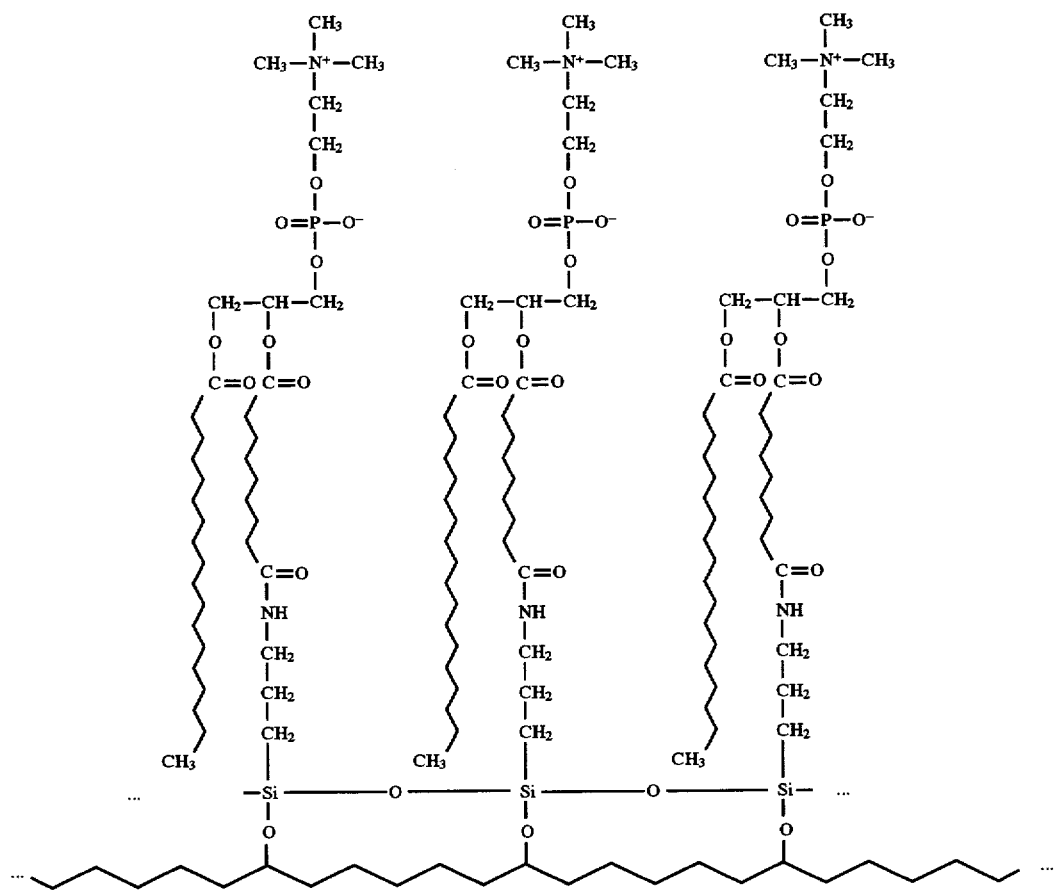

This covalent attachment can be accomplished by aminating the substrate, oxidizing the phospholipid, and combining the two in the presence of a carboxyl-reactive crosslinker, such as a carbodiimide, to form the amide linkage.

In particularly preferred embodiments, the present invention provides a method for improving the nonthrombogenic characteristics of a substrate by oxidizing a phospholipid compound having the following structure:

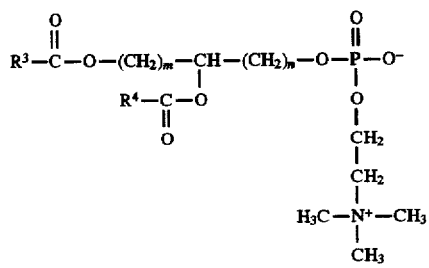

wherein: $R^3$ is a $(C_1-C_{30})$alkyl group having 0–4 double bonds; $R^4$ is a $(C_1-C_{30})$alkyl group having 0–4 double bonds; m is 1–4; n is 1–4; and either $R^3$ or $R^4$ has at least one double bond. The oxidation is carried out under conditions that selectively oxidize the at least one double bond in $R^3$ or $R^4$ of the phospholipid compound to form a carboxylated phospholipid. The resultant carboxylated phospholipid is then combined with an aminated substrate and a carboxyl-reactive crosslinker to form an amide linkage and covalently attach the phospholipid to the substrate. Suitable carboxyl-reactive crosslinkers are selected from the group consisting of 1-ethyl-3-(3-dimethylaminopropyl)-carbodiimide hydrochloride, N,N'-dicyclohexylcarbodiimide, 4-(p-azidosalicylamido)-butylamine, and diisopropylcarbodiimide.

In a particularly preferred embodiment, carboxylated phophatidylcholine is prepared by dissolving egg lecithin in a strong acid, e.g., an aqueous acetic acid solution, and adding an oxidizing agent capable of oxidizing a carbon-carbon double bond. The double bond is thereby converted to a carboxyl group (—COOH) as shown below:

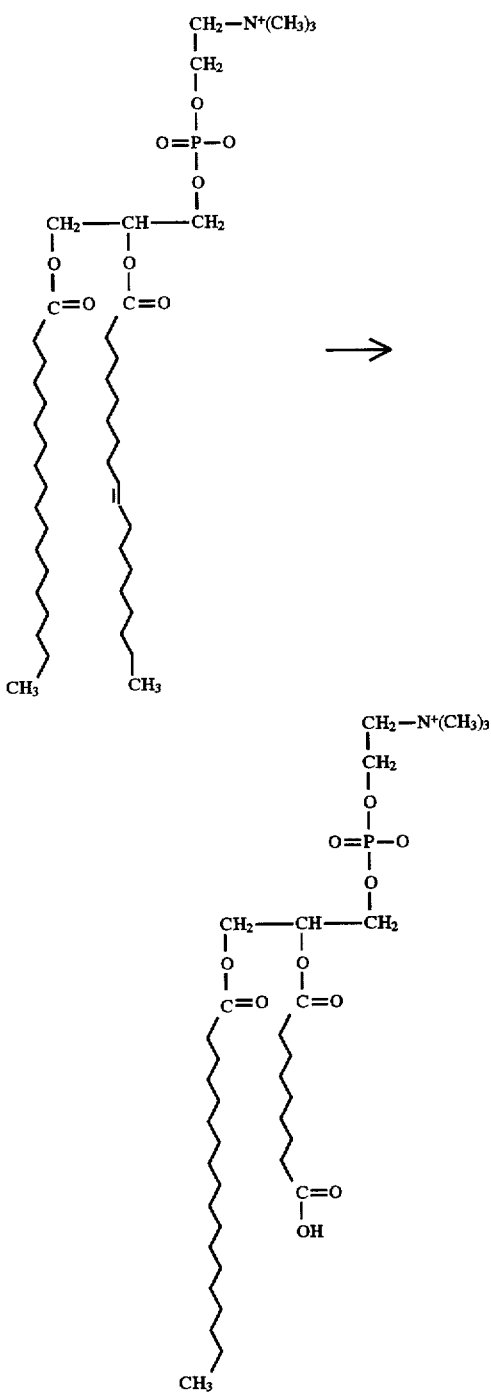

This carboxylated phosphatidylcholine is capable of being acted upon to form a covalent linkage with an appropriately modified substrate, e.g., an aminated substrate.

A substrate can be aminated by a variety of techniques depending on the substrate material. The coupling of the carboxylated phosphatidylcholine to the aminated substrate can be effectuated through the use of carbodiimide crosslinking agents, such as EDC (1-ethyl-3-(3-dimethylaminopropyl)carbodiimide), DIPCDI (diisopropyl carbodiimide), and the like. This type of crosslinking agent acts as a template to activate the carboxyl groups of the phospholipid moieties and the amine groups of the aminated substrate, thereby forming an amide linkage.

The above process illustrates the type of procedure by which various biocompatible materials may be coated with phosphatidylcholine in such a manner that the resulting material has reduced platelet adhesion and activation. The resulting biocompatible materials, when prepared in accordance with the invention, have demonstrable suppressed platelet adherence and reduced thrombogenicity. Suppressed platelet adherence and activation on the materials modified according to the invention may be demonstrated by standard procedures known in the art. For example, one technique is to expose treated materials to blood for a period of time sufficient for the blood proteins to react with the material, and subsequently rinsing with PBS and placing in a saline solution containing a fixing material, such as formaldehyde. Microscopy may be used to observe the surface clarity of the material in order to assess the adherence of blood components.

Medical devices in which the biocompatible material of the present invention can be incorporated include, but are not limited to, surgical implants, prostheses, and any artificial part or device which replaces or augments a part of a living body or comes into contact with bodily fluids, particularly blood. Various medical devices and equipment usable in accordance with the invention are known in the art. Examples of devices include catheters, suture material, tubing, and fiber membranes. Examples of catheters include central venous catheters, thoracic drain catheters, angioplasty balloon catheters. Examples of tubing include tubing used in extracorporeal circuitry, such as whole blood oxygenators. Examples of membranes include polycarbonate membranes, haemodialysis membranes, membranes used in diagnostic or biosensor devices. Also included are devices used in diagnosis, as well as polyester yarn suture material such as polyethylene ribbon, and polypropylene hollow fiber membranes.

Further illustrations of medical devices include the following: autotransfusion devices, blood filters, blood pumps, blood temperature monitors, bone growth stimulators, breathing circuit connectors, bulldog clamps, cannulae, grafts, implantible pumps, impotence and incontinence implants, intra-occular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, oxygenators, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, and vascular access devices.

Reasonable modifications and variations are possible from the foregoing disclosure without departing from either the spirit or scope of the present invention as defined by the claims. Objects and advantages of this invention will now be illustrated by the following examples, but the particular materials and amounts thereof recited in these examples, as well as other conditions and details, should not be construed to unduly limit this invention.

EXAMPLES

Example 1

Preparation of Phosphatidylcholine Starting Material

Initially, 500 mg of egg lecithin was dissolved in 50 ml of 90% acetic acid in a 500-ml Erlenmeyer flask. A 120-ml solution of an oxidizing reagent of 0.024M $KMnO_4$ and 0.04M $NaIO_4$ was prepared by combining 0.455 g of $KMnO_4$ in 60 ml of distilled $H_2O$ and 0.513 g of $NaIO_4$ in 60 ml of distilled $H_2O$. The oxidizing reagent was then added dropwise to the egg lecithin solution and gently stirred until the solution remained purple in color upon further addition of the oxidizing reagent (approximately 100 ml was added). The resulting solution was allowed to mix for 30 minutes. Subsequently, the solution was decolorized using 15 ml of 20% sodium bisulfite. The pH was then adjusted to 2.0 with 3M HCl. Extraction was performed with a chloroform/methanol 2:1 solution by adding 360 ml of the chloroform/methanol to a 500-ml Erlenmeyer flask. The resulting volume was then split into three polypropylene centrifuge bottles, each of a 250 ml capacity, and centrifuged at 3,000 rpm for 10 minutes. The top aqueous layer was removed, and the remainder divided between two bottles. The remaining phase was washed using 50 ml distilled $H_2O$ per bottle and a very small amount of NaCl so as to improve phase separation. The preparation was once again centrifuged at 3,000 rpm for 10 minutes. The upper phase was removed and discarded. A majority of the chloroform was removed from the resulting product phase using a rotary evaporator under vacuum. The temperature did not exceed 35° C.

Thin layer chromatography (TLC) analysis was used to verify the purity and identity of the carboxylated phosphatidylcholine. Initially, a small sample of starting egg lecithin and carboxylated phosphatidylcholine were dissolved in 2:1 chloroform/methanol solution. The sample was spotted onto Silica Gel GF glass plates (available from Analtech, Inc.), dried, and placed in a KOPLAN jar containing a developing system. The developing system used included chloroform/methanol/concentrated aqueous ammonia (65:35:8 by volume). The solvent front was allowed to migrate to within one inch of the top of the plate, removed, and then air-dried. Finally, the plate was placed in a jar containing iodine crystals and visualized. Retardation factor, $R_f$, was measured using the distance of solvent migration. The carboxylated lecithin had an $R_f$ value of 0.15, as compared to starting egg lecithin, which had an $R_f$ value of 0.040. The $R_f$ value was 0.15 for modified phosphatidylcholine (PC) and 0.40 for unmodified phosphatidylcholine. The product was stored in 50% dioxane/water solution for a 1.5 % solution at −20° C.

Example 2

Preparation of Aminopropylsilane Substrate

Glass cover slips were immersed in 3N HCl for 30 minutes. They were then rinsed with water and placed in 0.1M NaOH for 10 minutes. Subsequently, the slips were blotted dry and placed in a 50-ml PYREX dish. A 30ml solution of a 20% aminopropylsilane (APS) was added to the dish and the mixture remained for 30 minutes. APS was removed and the mixture was rinsed and subsequently placed in an oven at 110° C. under vacuum for 2 hours. The silica cover slips were aminated, possessing free amino groups on the surface.

Example 3

Preparation of Phosphatidylcholine-Grafted Material

First, the pH of the phosphatidylcholine starting material made according to Example 1 was adjusted to 5.0 using a dioxane solution and 0.1M NaOH. 1-Ethyl-3-(3-dimethylaminopropyl)carbodiimide (EDC, 340 mg) was added to a round-bottom flask containing the dioxane/phosphatidylcholine solution. The mixture was then added to a compartmentalized PYREX dish into four wells, containing the aminated cover slips prepared according to Example 2. The pH was then adjusted to 5.0. The dishes were then shaken on an orbital shaker at 100 rpm for 24 hours. The solvent was then removed, and the product was respectively rinsed with dioxane, methanol, NaCl and water in subsequent washings. The samples were allowed to dry and placed into separate vials.

Example 4

Analysis of Phosphatidylcholine-Modified Material

Verification of the modified material was performed using X-Ray Photoelectron Spectroscopy (XPS) analysis to identify phosphorous content of the grafted material. Either XPS or ESCA surface analysis techniques may be used to determine elemental and chemical composition of the top 2 to 20 layers of a solid sample. XPS has the capability of nondestructive depth-profiling in order to calculate phospholipid layer thickness. Materials were analyzed by XPS using the Perkin-Elmer Model 555 at a 45° incident angle. The surface area of the beam was 1 mm×3 mm with an average penetration depth of 50 Angstroms. Binding energy was measured by eV value. Corresponding eV positions were obtained for each sample, which was used to calculate the relative percent of each element found in the substrate.

The following Table summarizes the data which demonstrates both amination of surfaces using positive elemental analysis for nitrogen, and demonstrates grafting of phosphatidylcholine onto substrates using positive elemental analysis of phosphorous.

TABLE I

| XPS Atomic Concentration Table | | | | | |
|---|---|---|---|---|---|
| Substrate | % N | % P | % C | % Si | % O |
| Glass | 1.2 | 0 | 17 | 24 | 56 |
| Si wafer | 1.1 | 0 | 14 | 40 | 45 |
| Quartz | 1.5 | 0 | 24 | 25 | 49 |
| $NH_2$-Glass | 3.9 | 0 | 25 | 21 | 47 |
| $NH_2$—Si wafer | 3.3 | 0 | 27 | 32 | 36 |
| $NH_2$-Quartz | 4.1 | 0 | 28 | 23 | 43 |
| Phophatidylcholine-Glass (side 1) | 3.6 | 0.73 | 60.5 | 12.1 | 22.9 |
| Phophatidylcholine-Glass (side 2) | 4.2 | 0.68 | 66.0 | 8.1 | 20.9 |

As can be seen from the data in Table I, the phosphatidylcholine is covalently bound to the surface material. The carbon content increased dramatically upon grafting the phosphatidylcholine due to the presence of lengthy fatty acid chains. Oxygen and silica contents decreased because the bulk of oxygen and silica were not subject to the incident X-rays due to the phospholipid occupancy of the top 50 Angstroms. The nitrogen content increased with amination of the surface. The presence of phosphorous in the phosphatidylcholine-grafted surface indicated successful grafting of phosphatidylcholine onto the surface material.

Example 5

Atomic Force Microscopy Analysis of Modified Surface Materials

Atomic Force Microscopy (AFM) analysis was used to demonstrate the different surface morphologies for different samples of unmodified and materials modified according to the invention. The topography of the synthesized materials was analyzed using NANOSCOPE III (available from Digital Instruments).

Roughness analysis was obtained from these samples: glass, hydrated glass, aminated glass, hydrated and aminated glass, phosphatidylcholine-grafted glass, hydrated phosphatidylcholine-grafted glass. The samples were analyzed in air and water, from which surface plots were constructed. Surface plots displayed the selected image with color-coded height information in a three-dimensional oblique perspective, from which roughness parameters were calculated. RMS value is the standard deviation of the difference between the highest and lowest points within a given area (Z values). The following Table shows the roughness values for the same samples as listed above.

TABLE II

Roughness Values from AFM Analysis

| Material | RMS @ 1.0 $\mu^2$ | RMS @ 4.0 $\mu^2$ |
| --- | --- | --- |
| Glass | 0.628 | 0.938 |
| Hydrated glass | 0.210 | 0.244 |
| Aminated glass | 0.652 | 1.1175 |
| Hydrated aminated glass | 0.325 | 0.673 |
| Phophatidylcholine-glass | 6.555 | 7.241 |
| Hydrated phophatidylcholine-glass | 1.601 | 1.664 |

As can be seen from the above data, phosphatidylcholine-grafted glass is the "roughest" surface when nonhydrated. Upon hydration, the RMS value of phosphatidylcholine-grafted glass decreased four-fold. In comparison, the hydrated glass RMS value decreased three-fold, and the aminated glass surface RMS value decreased two-fold. Therefore, upon exposure to water, the phosphatidylcholine-grafted glass surface exhibited a substantial decrease in surface roughness.

Example 6

Surface Characteristics using Contact Angle Analysis

Contact angle analysis demonstrates the nature of surface materials, which is used to illustrate and compare the physical properties of modified and unmodified surface materials. Advancing and receding contact angles were recorded for glass, aminated glass, and phosphatidylcholine-glass using an NRL C.A. GONIOMETER (Rame-hart, Inc., Model #100-00115) with 0.08 ml droplet volume. The resulting data is shown below in the Table III.

TABLE III

| Material | Contact Angle Data Advancing Contact Angle | Receding Contact Angle |
| --- | --- | --- |
| Glass | | |
| Average: | 52.7 ± 3.0 (n = 9) | 32.0 ± 1.7 (n = 6) |
| Aminated Glass | | |
| Average: | 70.6 ± 0.76 (n = 12) | 34.8 ± 1.4 (n = 8) |
| Phophatidylcholine-Glass | | |
| XPS P/C ratio: 0.009 Average: | 67.0 ± 5.7 (n = 9) | 13.5 ± 2.0 (n = 6) |
| Phophatidylcholine-Glass | | |
| XPS P/C ratio: 0.018 Average: | 58.1 ± 3.2 (n = 9) | 8.8 ± 4.2 (n = 6) |

As can be seen from the data in the above table, the droplet front from the glass and animated glass samples was smooth and uniform. However, the contact angle measurements of the phosphatidylcholine-grafted glass sample exhibited a stick/slip phenomenon, which indicates nonuniformity at a microscopic level.

The significant differences between the receding contact angles of the samples suggest that the phosphatidylcholine-grafted glass has a unique interaction with water. The low receding contact angle of 8.8° indicates a strong affinity of the phosphatidylcholine-grafted glass for water. Aminated glass and unmodified glass surfaces had receding contact angles of 32 and 35 respectively, indicating interactions with water identical to each other. Hence, the phosphatidylcholine grafted glass surface has physical and chemical properties which are distinct from the other materials.

Example 7

Demonstration of Suppressed Platelet Adherence and Thrombogenicity

The differences in cell behavior toward materials modified according to the invention were examined by measuring platelet adherence to the modified surfaces of materials as compared to unmodified surfaces when exposed to blood. Whole blood was drawn from human donors, and nine parts whole blood was mixed with one part citrate citric dextrose (CCD) containing 3.50 ml of 0.1M citric acid, 46.50 ml of 0.1 citrate, and 1.25 g of dextrose at pH 6.5. The resulting solution was centrifuged at 800 rpm in a SORVALL table-top centrifuge for 20 minutes at room temperature. Subsequently, the platelet-rich plasma (PRP) was removed from the red and white blood cell portions. The samples (i.e., underivatized glass, aminated glass, and phosphatidylcholine-glass) were placed in a PYREX dish. Added to each of the samples was 160 microliters of the platelet-rich plasma using EPPENDORF micropipets. The solutions stood for approximately 20 minutes. The plasma was then removed and the samples were rinsed with phosphate buffered saline (PBS). The samples were fixed using 3.7% formaldehyde for 15 minutes and rinsed with PBS. The samples were stained with Coomassie Brilliant Blue (CBB) for 90 minutes, destained, rinsed, and mounted on a slide.

Materials modified in accordance with the invention, including glass, Si wafer, and quartz, were exposed to whole blood for 20 minutes. The blood was subsequently removed from the exposed materials. The materials were then rinsed twice with PBS and placed in a saline solution containing formaldehyde as a fixing agent for the biological components remaining on the materials. The materials were then examined for surface clarity using standard microscopy techniques.

Platelet number, spread area, and averages thereof were calculated by collecting several images of materials exposed to the platelet adhesion assay. Several images were taken of each sample which had been exposed to the platelet adhesion assay using OPTIMUS Imaging Software (obtained from BioScan, Edmonds, Wash.). The number of platelets was then calculated for the different materials.

Figure 2:
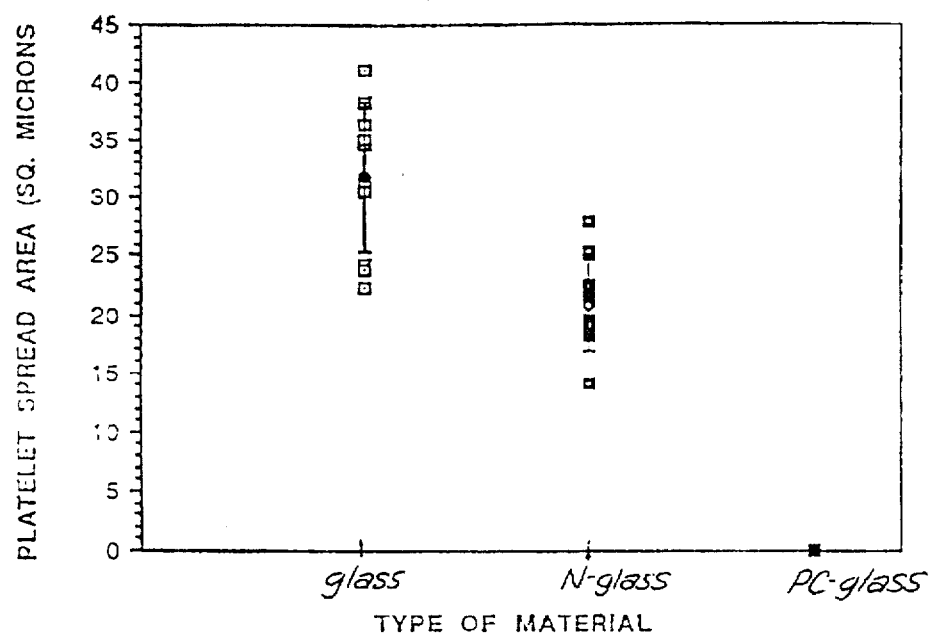
FIG. 2 illustrates comparative spread platelet area for the various materials, both unmodified and modified according to the invention. The substrates are glass, aminated glass (N-glass), and phosphatidylcholine-grafted glass (PC-glass).

FIG. 1 is a graph illustrating comparative platelet adhesion (number of platelets per unit area) to various material substrates. In contrast to the unmodified material and the aminated material, the phosphatidylcholine-modified glass surfaces (XPS P/C ratio was 0.018) exhibited minimal platelet adhesion. FIG. 2 and Table IV shows the comparative platelet spread results for unmodified and modified materials in accordance with the invention. The data demonstrates the minimal platelet adhesion and platelet spread of phosphatidylcholine-grafted materials.

TABLE IV

| Platelet Spread Data | | |
|---|---|---|
| Material | Adherent Platelets | Spread Area ($\mu^2$) |
| Glass | 61.6 ± 11.37 | 31.8 ± 6.5 |
| Aminated Glass | 73.9 ± 11.4 | 20.82 ± 3.90 |
| Phophatidylcholine-Glass | 0 | 0 |

As can be seen from the data in the above table and FIGS. 1 and 2, phosphatidylcholine-grafted glass had negligible platelet adhesion and virtually no platelet spreading.

Example 8

Other Materials Grafted with Phosphatidylcholine

Polypropylene

The process of preparing the phosphatidylcholine-linked composition was carried out in accordance with the invention, but instead the surface material used was polypropylene (PP). Unmodified polypropylene and animated polypropylene (having 0.6–0.8 nmol/cm$^2$ NH$_2$ groups) was obtained from Neomecs, Inc., St. Louis Park, Minn. Polypropylene with adsorbed phosphatidylcholine was obtained by subjecting unmodified polypropylene to the coupling procedure described in Example 3 (without the amine modified surface, the procedure simply resulted in adsorbed, rather than covalently linked, phosphatidylcholine). Aminated polypropylene with covalently linked phosphatidylcholine was obtained in the manner described in Example 3.

The resulting products were comparatively tested using standard microscopy techniques. When compared to unmodified polypropylene surfaces or polypropylene surfaces modified according to different methods, the comparative test results demonstrated that other substances, such as polypropylene, is also receptive to the process of the invention and likewise suppresses platelet adhesion. See FIG. 3 and Table V below.

TABLE V

| Platelet Adhesion Data | | |
|---|---|---|
| Material | Adherent Platelets | Spread Area (microns) |
| polypropylene with absorbed phophatidylcholine (PP-Ads-PC) | 81 ± 13 | 25.6 ± 3.6 |
| phophatidylcholine linked to aminated polypropylene (PP-N-PC) | 10 ± 6 | 26.4 ± 7.1 |
| polypropylene (PP) | 63 ± 9 | 30.0 ± 5.2 |
| aminated polypropylene (PP-N) | 138 ± 7 | 13.8 ± 4.4 |

Figure 3:
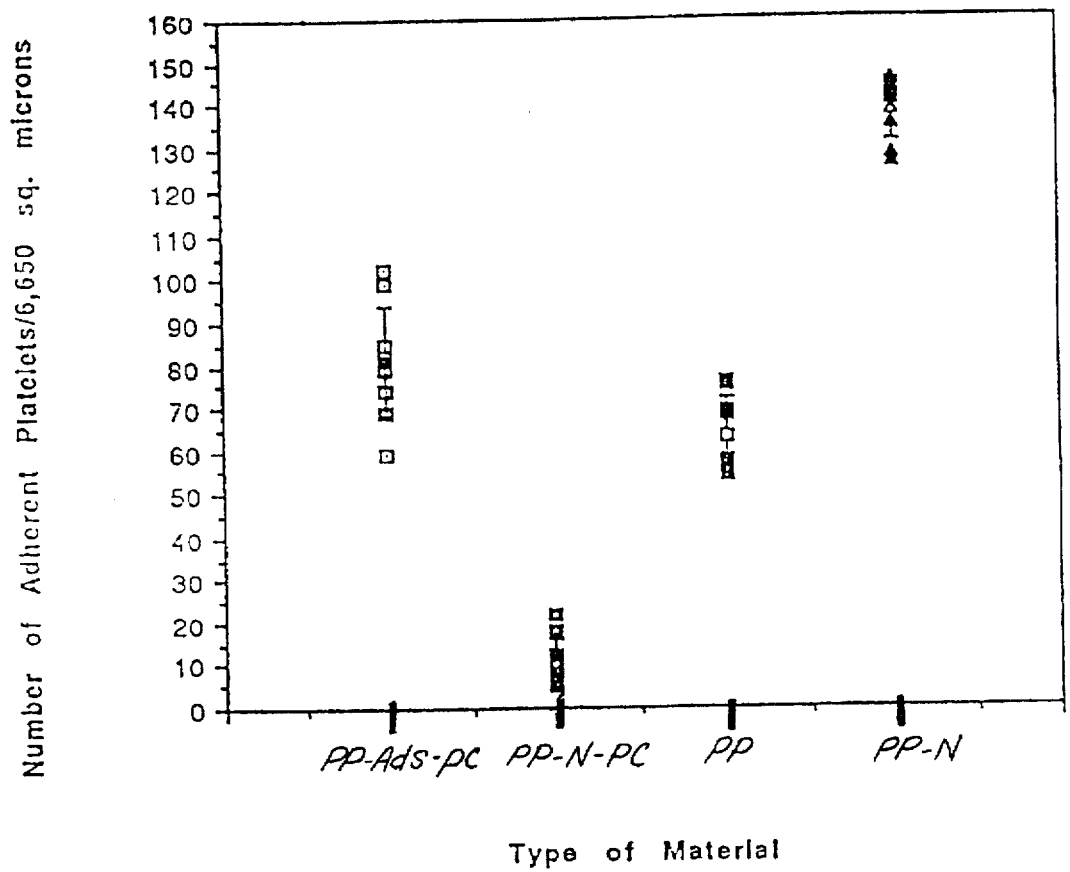
FIG. 3 is a graph illustrating the number of platelets adherent to unmodified polypropylene samples as compared to modified polypropylene in accordance with the coupling process of the invention. The substrates are polypropylene (PP), aminated polypropylene (PP-N), phosphatidylcholine adsorbed onto polypropylene (PP-Ads-PC) and phosphatidycholine grafted onto polypropylene (PP-N-PC).
Figure 4A:
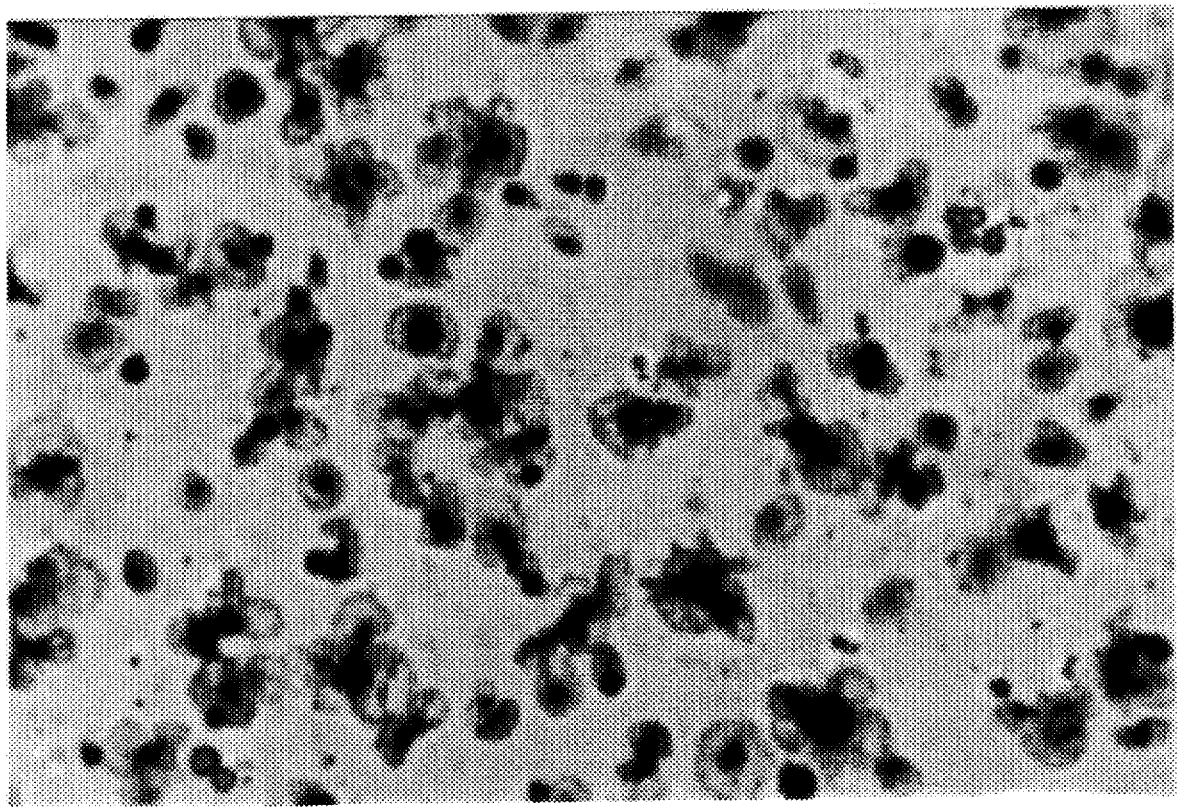
FIG. 4A is a photograph of adherent platelets on polypropylene-adsorbed phosphatidylcholine (PP-Ads-PC).
Figure 4B:
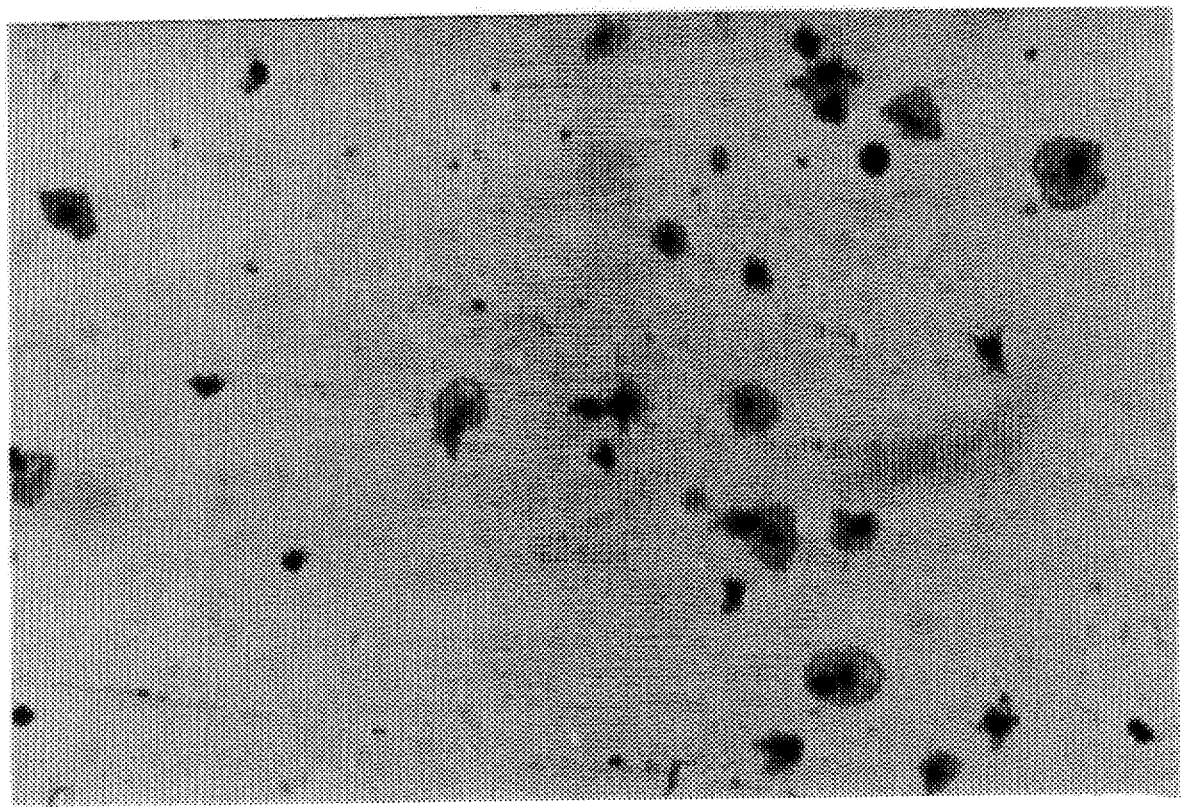
FIG. 4B is a photograph of adherent platelets on phosphatidylcholine covalently linked to polypropylene (PP-N-PC).
Figure 4C:
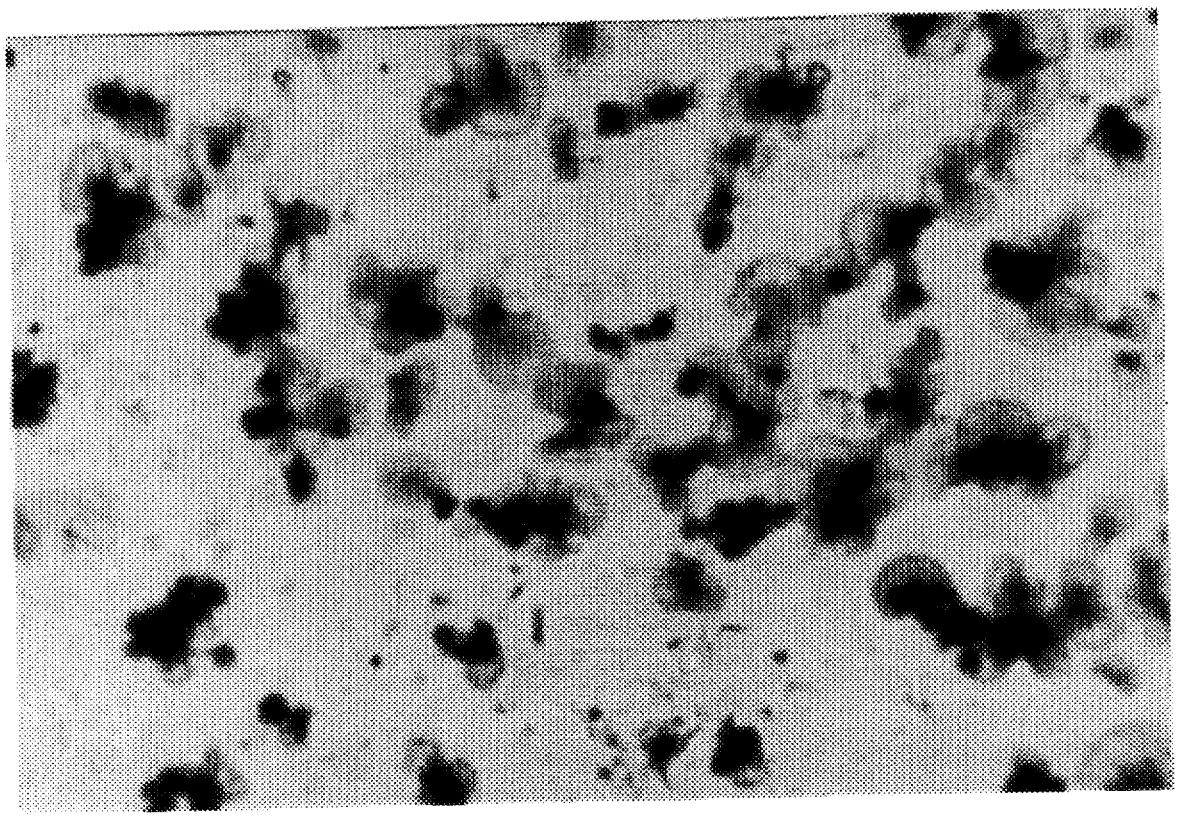
FIG. 4C is a photograph of adherent platelets on polypropylene (PP).
Figure 4D:
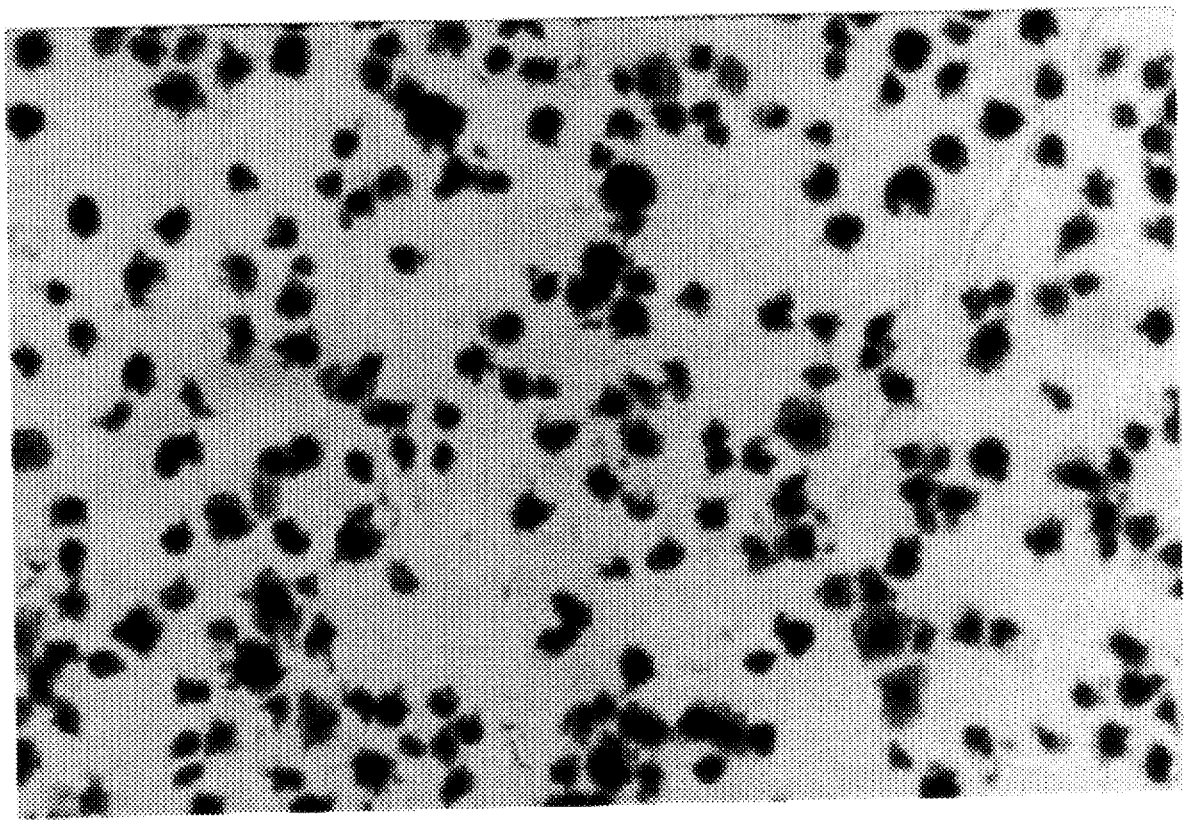
FIG. 4D is a photograph of adherent platelets on aminated polypropylene (PP-N).

As can be seen from the platelet adhesion data in the above table and FIG. 3, the phosphatidylcholine-polypropylene showed suppressed platelet adhesion. FIGS. 4A through 4D are photographs of the above surfaces which depict surface characteristics consistent with the above data (FIG. 4A=PP-Ads-PC; FIG. 4B=PP-N-PC; FIG. 4C=PP; FIG. 4D=PP-N).

Polytetrafluoroethylene

The same experiment as above was performed, but instead the substrate material used was polytetrafluoroethylene. Unmodified polytetrafluoroethylene and aminated polytetrafluoroethylene (having 0.8 nmol/cm$^2$NH$_2$ groups) was obtained from Neomecs, Inc., St. Louis Park, Minn. Aminated polytetrafluoroethylene with covalently linked phosphatidylcholine was obtained in the manner described in Example 3.

Figure 5:
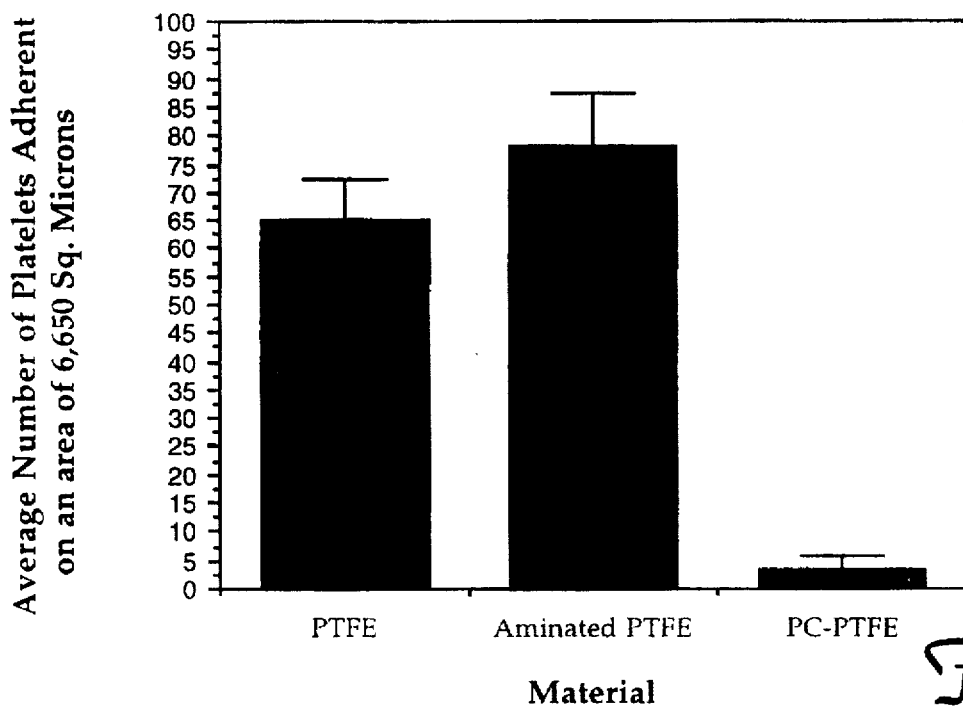
FIG. 5 is a graph illustrating the number of platelets adherent to unmodified polytetrafluoroethylene (PTFE), aminated PTFE and PTFE modified with phosphatidylcholine.

The graph illustrating platelet adhesion on polytetrafluoroethylene is shown in FIG. 5. As can be seen from FIG. 5, polytetrafluoroethylene likewise demonstrated reduced platelet adhesion onto the surface when prepared in accordance with the invention, as compared to both aminated polytetrafluoroethylene and unmodified polytetrafluoroethylene alone. These results show that phosphatidylcholine can be grafted onto various substrate materials and are capable of obtaining the desired biocompatibility characteristics of the invention.

Example 9

Albumin Adsorption and Fibrinogen Adsorption

Albumin and fibrinogen are plasma proteins that adsorb to material surfaces and influence blood compatibility. The adsorption of albumin and fibrinogen on glass, animated glass, and phosphatidylcholine-grafted glass was therefore measured.

Albumin Adsorption

Radio-labeled albumin, $^{125}$I-BSA (available from Sigma), was used in concentrations 0.009, 0.15, 0.9, and 1.5 mg BSA/ml, with a 45:1 ratio of BSA/$^{125}$I-BSA. Replicate samples of underivatized glass, animated glass and PC-glass samples were placed in FALCON 24-well plates, to each sample was added 250 microliters of heated BSA solution. The plates were incubated at 37° C. for 2 hours. Subsequently, the samples were aspirated and rinsed with four subsequent washings of PBS. The samples were then removed from the plate and placed in individual scintillation vials. To each sample was added 5 ml scintillation cocktail and the samples were counted using a BECKMAN LS 6500 Scintillation Counter. After 24 hours, the cocktail was removed from the vials and transferred to separate scintillation vials for counting. The original samples were exposed to 5 ml of 1% SDS solution for 24 hours. After incubation, the SDS was removed from the samples and counted. To the remaining samples was added 5 ml of scintillation cocktail and these samples were then counted.

Figure 6:
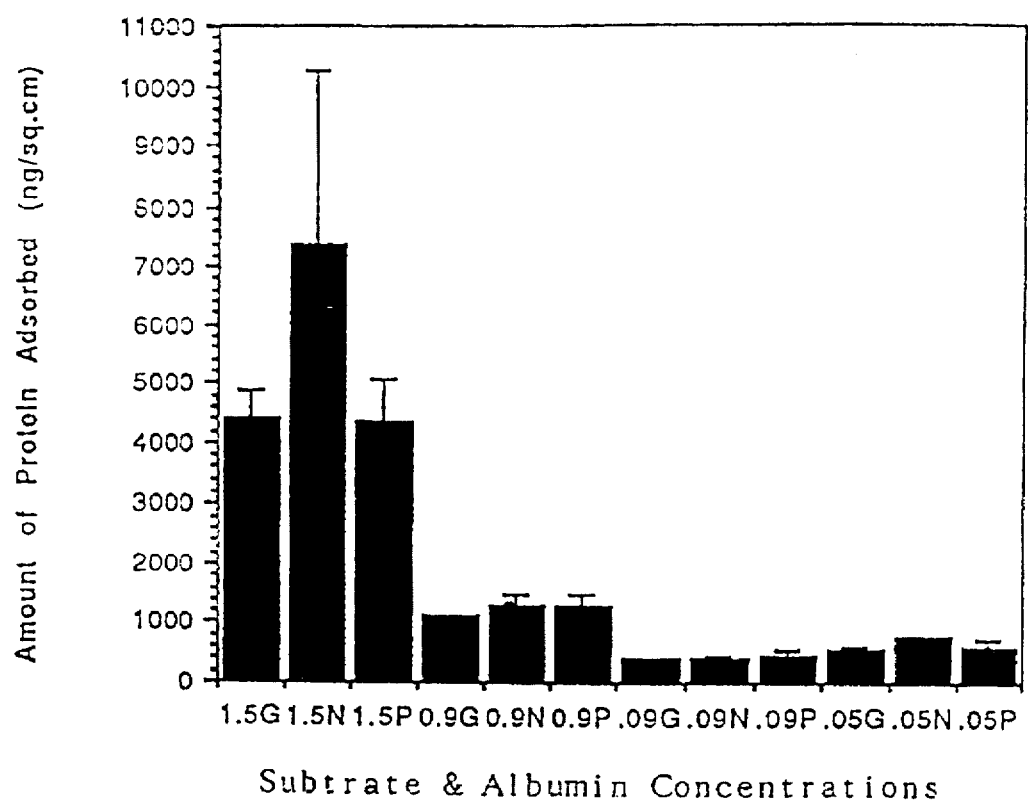
FIG. 6 is a graph illustrating albumin (BSA) adsorption on various materials.

FIG. 6 is a graph illustrating albumin (BSA) adsorption after 2 hours of incubation on glass (G), aminated glass (N), and phosphatidylcholine covalently linked to glass (P) at several albumin concentrations including 1.5 mg/ml, 0.9 mg/ml, 0.09 mg/ml, and 0.005 mg/ml. As can be seen from FIG. 6, there is no preferential adsorption of albumin to phosphatidylcholine-grafted glass surfaces.

Figure 7:
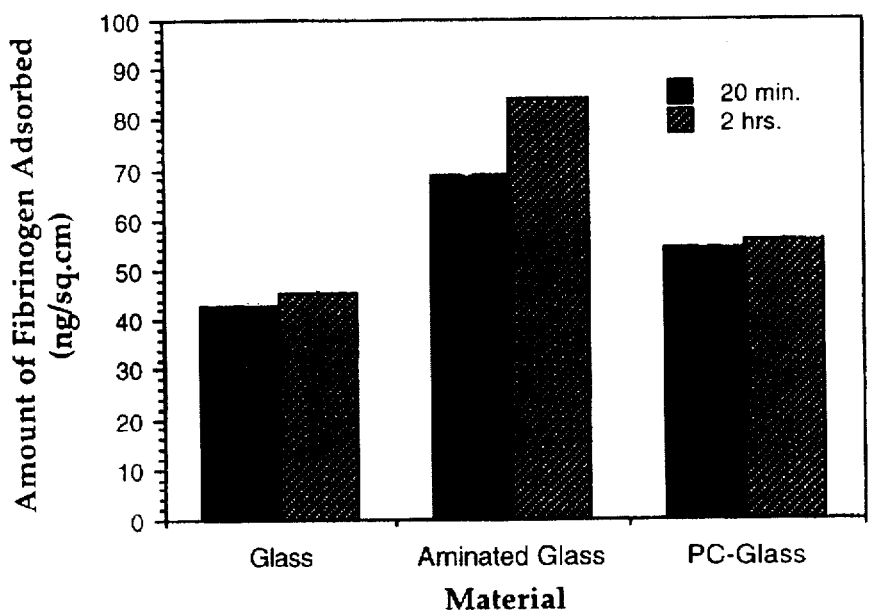
FIG. 7 is a graph containing fibrinogen adsorption assay data for various materials, indicating the amount of adsorbed fibrinogen.

Fibrinogen Adsorption $^{125}$I-Fibrinogen (human fibrinogen available from ICN, Irvine, Calif.) adsorption to the test surfaces was measured from 1.0% human plasma in Tris buffer at a pH of 7.4. The $^{125}$I-Fibrinogen used had a specific activity of 4.15 mCi/mg and a concentration of 0.851 mCi/ml. To 70 microliters of platelet poor plasma was added 24 microliters of $^{125}$I-Fibrinogen and subsequently diluted using 7 ml Tris buffer. Triplicate samples of glass, aminated glass, and PC-glass were placed in FALCON 24-well plates, and 300 microliters of the fibrinogen solution was added to each sample. The samples were then incubated at room temperature for 2 hours and 20 minutes. The fibrinogen solution was removed and then samples were washed three times with Tris buffer. The samples were then placed into glass scintillation vials and 5 ml of scintillation cocktail was added to each vial. The samples were then counted with a BECKMAN LS 6500 Scintillation Counter. FIG. 7 is a graph illustrating fibrinogen adsorption assay results.

Example 10

Complement Activation Assay

Complement activation assays are useful in determining the compatibility of various substances with the immune system. The degree to which complement enzymes are activated by contact with a foreign material can be measured, thereby indicating the corresponding response of the immune system to that material. Blood from human donors was drawn into sterile heparin-containing tubes. Heparinized blood was tested on several samples, including glass, aminated glass and PC-glass. Controls were run with no materials present. The samples were incubated in 50-ml polypropylene tubes at 37° C. for 10 to 30 minutes. Subsequently, EDTA was added to individual centrifuging tubes and aliquots were frozen at −70° C.

Figure 8:
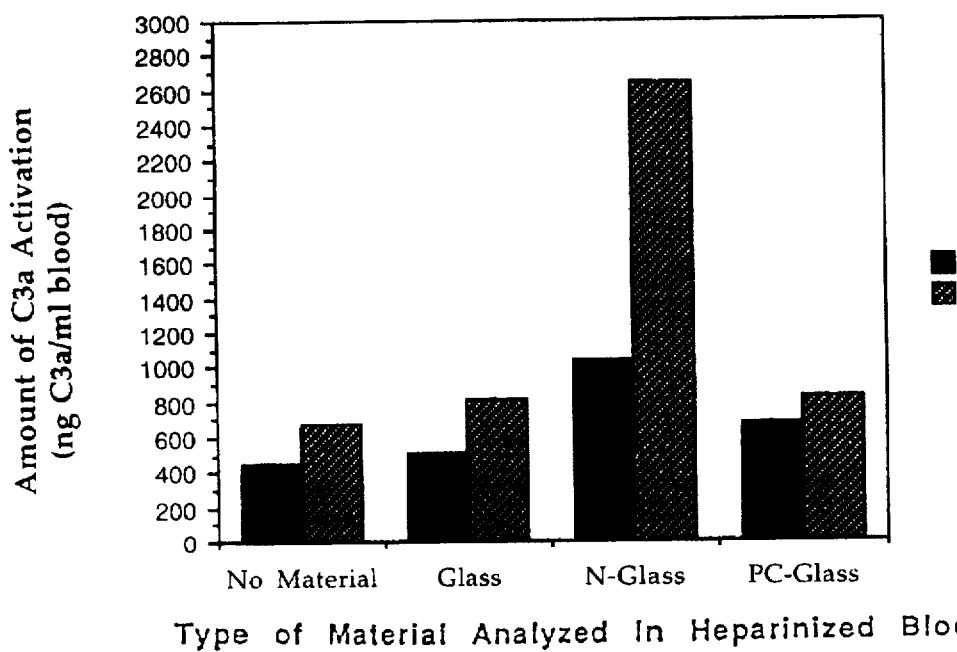
FIG. 8 shows comparative data from a Heparinized Blood Complement Activation Assay using various materials.

Complement activation was determined utilizing the AMERSHAM standard human complement C3a activation radioimmunoassay kit. Samples of glass, aminated glass, and phospholipid-grafted glass were measured for C3a activation in heparinized blood. Complement protein adsorption on the samples was evaluated using radiolabeled antibodies specific for C3a des Arg. As can be seen from FIG. 8, there was no elevation in complement activation on the phophatidylcholine-modified glass as compared to the level of activation seen when no material was present. On the other hand, the aminated glass demonstrated significant complement activation.

The complete disclosures of all patents, patent applications, and publications are incorporated herein by reference as if each were individually incorporated by reference. The invention has been described with reference to various specific and preferred embodiments and techniques. However, it should be understood that many variations and modifications may be made while remaining within the spirit and scope of the invention.

What is claimed is:

1. A biocompatible material comprising a substrate and a phospholipid moiety covalently attached thereto in an amount and orientation effective to provide an improved nonthrombogenic surface relative to the substrate without the phospholipid moiety covalently attached thereto, wherein the biocompatible material has the following structure:

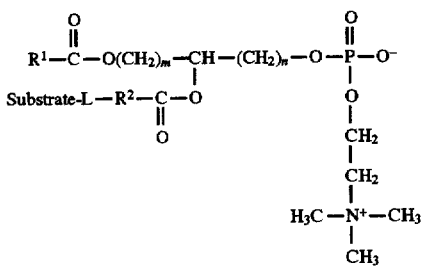

wherein:

(a) $R^1$ is a $(C_1-C_{30})$alkyl group;

(b) $R^2$ is a $(C_1-C_{30})$alkylene group;

(c) m is 1–4;

(d) n is 1–4; and (e) L is —C(O)—NH—$(CH_2)_p$— wherein p is 0–20.

2. The biocompatible material of claim 1 wherein:

(a) $R^1$ is a $(C_{12}-C_{20})$alkyl group;

(b) $R^2$ is a $(C_4-C_{10})$alkylene group;

(c) m is 1; and (d) n is 1.

3. The biocompatible material of claim 1 wherein L is —C(O)—NH—$(CH_2)_p$— wherein p is 1–6.

4. The biocompatible material of claim 1 wherein the substrate is an organic polymer.

5. The biocompatible material of claim 4 wherein the organic polymer is selected from the group consisting of polypropylene and polytetrafluoroethylene.

6. A medical device comprising the biocompatible material of claim 1.

7. A method for enhancing the biocompatibility of a substrate comprising:

(a) covalently attaching a phospholipid compound to the substrate with a linker of the formula —C(O)—NH—$(CH_2)_p$—, wherein p is 0–20, in an amount and orientation effective to provide an improved nonthrombogenic surface relative to the substrate without the phospholipid moiety covalently attached thereto; and (b) contacting the substrate with blood; wherein the phospholipid moiety has the following structure:

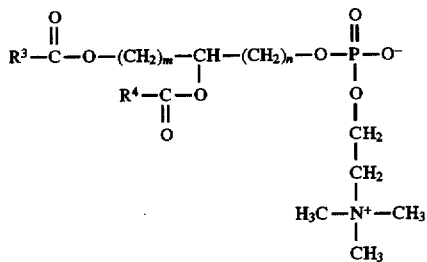

wherein:

(a) $R^3$ is a $(C_1-C_{30})$alkyl group having 0–4 double bonds;

(b) $R^4$ is a $(C_1-C_{30})$alkyl group having 0–4 double bonds;

(c) m is 1–4;

(d) n is 1–4; and (e) either $R^3$ or $R^4$ has at least one double bond.

8. The method of claim 7 wherein the substrate is an aminated substrate and the phospholipid compound is covalently attached to the aminated substrate by:

(a) oxidizing the at least one double bond in $R^3$ or $R^4$ of the phospholipid compound to form a carboxylated phospholipid; and (b) combining the carboxylated phospholipid with the animated substrate and a carboxyl-reactive crosslinker to form an amide linkage and covalently attach the phospholipid to the substrate.

9. The method of claim 8 wherein the carboxyl-reactive crosslinker is selected from the group consisting of 1-ethyl-3-(3-dimethylaminopropyl)-carbodiimide hydrochloride, N,N'-dicyclohexylcarbodiimide, 4-(p-azidosalicylamido)-butylamine, and diisopropylcarbodiimide.

10. The method of claim 7 wherein the substrate is an organic polymer.

11. The method of claim 10 wherein the organic polymer is selected from the group consisting of polypropylene and polytetrafluoroethylene.

12. The method of claim 10 wherein the substrate having improved biocompatibility is contained in a medical device.

13. A biocompatible material comprising a substrate and a phospholipid moiety covalently attached thereto in an amount and orientation effective to provide an improved nonthrombogenic surface relative to the substrate without the phospholipid moiety covalently attached thereto, having the following structure:

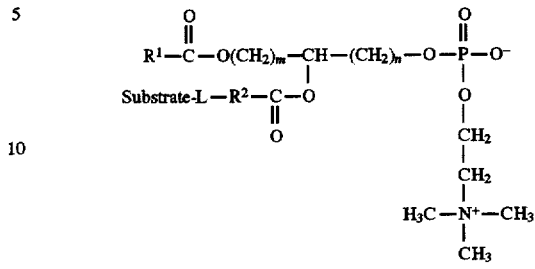

wherein:

(a) $R^1$ is a $(C_1-C_{20})$ alkyl group;

(b) $R^2$ is a $(C_4-C_{10})$ alkylene group;

(c) m is 1;

(d) n is 1; and (e) L is —C(O)—NH—$(CH_2)_p$— wherein p is 1–6.

* * * * *

UNITED STATES PATENT AND TRADEMARK OFFICE
CERTIFICATE OF CORRECTION

Page 1 of 2

PATENT NO.: 5,711,959
DATED: January 27, 1998
INVENTOR(S): Anja S. Kohler et al.

It is certified that error appears in the above-identified patent and that said Letters Patent is hereby corrected as shown below:

On the title page item [56]

under Foreign Patent Documents, delete "92/06719 4/1992 United Kingdom" and insert --WO92/06719 4/1992 WIPO--;

Page 2, under Other Publications, insert "Charles Pidgeon et al., "Immobilized Artificial Membrane Chromatography: Supports Composed of Membrane Lipids," Anaytical Biochemistry", 176, 36-47 (1989)--;

Col. 12, line 54, delete "phophatidylcholine" and insert --phosphatidylcholine--;
Col. 12, line 55, delete "phophatidylcholine" and insert --phosphatidylcholine--;
Col. 13, line 38, delete "phophatidylcholine" and insert --phosphatidylcholine--;
Col. 13, line 39, delete "phophatidylcholine" and insert --phosphatidylcholine--;
Col. 14, line 12, delete "phophatidylcholine" and insert --phosphatidylcholine--;
Col. 14, line 15, delete "phophatidylcholine" and insert --phosphatidylcholine--;
Col. 14, line 21, delete "animated" and insert --aminated--;
Col. 15, line 31, delete "phophatidylcholine" and insert --phosphatidylcholine--;
Col. 15, line 48, delete "animated" and insert --aminated--;
Col. 16, line 8, delete "phophatidylcholine" and insert --phosphatidylcholine--;

UNITED STATES PATENT AND TRADEMARK OFFICE
CERTIFICATE OF CORRECTION

PATENT NO. : 5,711,959
DATED : January 27, 1998
INVENTOR(S) : Anja S. Kohler et al.

It is certified that error appears in the above-identified patent and that said Letters Patent is hereby corrected as shown below:

Col. 16, line 9, delete "phophatidylcholine" and insert --phosphatidylcholine--;

Col. 16, line 25, delete "nmol/cm$^2$NH$_2$" and insert --nmol/cm$^2$ NH$_2$--;

Col. 16, line 45, delete "animated" and insert --aminated--;

Col. 16, line 52, delete "animated" and insert --aminated--; and

Col. 19, line 8 (claim 8), delete "animated" and insert --aminated--.

Signed and Sealed this

Eighth Day of June, 1999

Attest:

Attesting Officer

Q. TODD DICKINSON

Acting Commissioner of Patents and Trademarks